United States Patent [19]

Drees et al.

[11] Patent Number: 5,932,953
[45] Date of Patent: Aug. 3, 1999

[54] METHOD AND SYSTEM FOR DETECTING MATERIAL USING PIEZOELECTRIC RESONATORS

[75] Inventors: Dennis M. Drees, Schaumburg, Ill.; Howard R. Shanks; Richard A. Van Deusen, both of Ames, Iowa; Allen R. Landin, Boone, Iowa

[73] Assignee: Iowa State University Research Foundation, Inc., Ames, Iowa

[21] Appl. No.: 08/884,991

[22] Filed: Jun. 30, 1997

[51] Int. Cl.$^6$ .................................................. H01L 41/08
[52] U.S. Cl. .......................... 310/324; 310/312; 310/321; 310/316; 310/334
[58] Field of Search ................................ 310/312, 316, 310/319, 321, 324, 334; 73/23.2, 23.4, 23.28, 24.01, 24.05, 24.06, 25.05, 30.01, 30.03, 30.04, 31.05, 31.06, 54.41

[56] References Cited

U.S. PATENT DOCUMENTS

| | | | |
|---|---|---|---|
| 3,200,271 | 8/1965 | Haines | 310/312 X |
| 3,561,253 | 2/1971 | Dorman | 310/324 X |
| 3,653,253 | 4/1972 | Olin | 73/28 |
| 3,879,992 | 4/1975 | Bartera | 73/23 X |
| 4,236,893 | 12/1980 | Rice | 23/230 |
| 4,312,228 | 1/1982 | Wohltjen | 73/23 X |
| 4,540,981 | 9/1985 | Lapetina et al. | 310/321 X |
| 4,719,383 | 1/1988 | Wang et al. | 310/324 |
| 4,735,906 | 4/1988 | Bastiaans | 436/527 |
| 4,789,804 | 12/1988 | Karube et al. | 310/321 X |
| 4,841,775 | 6/1989 | Ikeda et al. | 310/324 X |
| 4,988,957 | 1/1991 | Thompson et al. | 358/624 |
| 5,075,641 | 12/1991 | Weber et al. | 310/324 X |
| 5,162,691 | 11/1992 | Mariani et al. | 310/321 |
| 5,185,589 | 2/1993 | Krishnaswamy et al. | 310/324 X |
| 5,231,327 | 7/1993 | Ketcham | 310/366 |
| 5,233,259 | 8/1993 | Krishnaswamy et al. | 310/324 |
| 5,367,308 | 11/1994 | Weber | 343/700 |
| 5,404,628 | 4/1995 | Ketcham | 29/25.35 |
| 5,668,303 | 9/1997 | Giesler et al. | 73/24.06 |

FOREIGN PATENT DOCUMENTS 2078184  3/1993  Canada.

OTHER PUBLICATIONS

Low–temperature coefficient bulk acoustic wave composite resonators; J.S. Wang and K.M. Lakin; Appl. Phys. Lett. vol. 10, No. 1, 1982, pp. 308–309.

Equivalent Circuit Modeling of Stacked Crystal Filters; K.M. Lakin; Proc 35th Ann. Freq. Control Symposium; May 1981; pp. 257–262.

Sputtered C–Axis Inclined Piezoelectric Films And Shear Wave Resonators; J.S. Wang, K.M. Lakin and A.R. Landin; IEEE 1983 Ultrasonics Symposium Proceeding.

Fundamental–Mode Pierce Oscillators Utilizing Bulk–Acoustic–Wave Resonators in the 250–300– MHz Range; Stanley G. Burns and Richard S. Ketcham; IEEE Transactions on Microwave Theory and Techniques; vol. MT–32, No. 12; Dec. 1984, pp. 1668–1671.

Thin Film Resonator Based Low Insertion Loss Filters; K.M. Lakin, G.R. Kline, R.S. Ketcham, and S.G. Burns; IEEE 1986 Ultrasonic Symposium Proceeding.

(List continued on next page.)

Primary Examiner—Mark O. Budd
Attorney, Agent, or Firm—Leydig, Voit & Mayer, Ltd.

[57] ABSTRACT

A method and system for detecting material bound on a surface of a piezoelectric resonator introduces a signal of a constant frequency through the sensing resonator and detects a change in the insertion phase shift of the resonator as a result of the binding of the material being detected on the surface of the resonator. Environmental effects on the measurement are effectively canceled by the use of a reference resonator driven by the same input signal. A multiple-port sensing device is provided which includes thin-film sensing and reference resonators monolithically formed on a substrate.

37 Claims, 4 Drawing Sheets

OTHER PUBLICATIONS

Low Insertion Loss Filters Synthesized With Thin Film Resonators; G.R. Kline, R.S. Ketcham, and K.M. Lakin; 1987 Ultrasonics Symposium Proceeding, pp. 375–380.

Thin Film Resonator Technology; K.M. Lakin, G.R. Kline, R.S. Ketcham, A.R. Landin, W.A. Burkland, K.T. McCarron, S.D. Braymen, and S.G. Burns; 41st Annual Frequency Control Symposium—1987, pp. 371–381.

Growth and Characterization of Aluminum Nitride Thin Films for Piezoelectric Devices; K. T. McCarron, G.R. Kline, J.T. Martin, D.S. Robinson, R. Shinar, and K.M. Lakin; Paper Presented at the 1988 Ultrasonic Symposium.

A Thin–Film Bulk–Acoustic–Wave Resonator–Controlled Oscillator on Silicon; W.A. Burkland, A.R. Landin, and R.S. Ketcham; IEEE Electron Device Letters, vol. EDL–8, No. 11, Nov. 1987, pp. 531–533.

Thin Film Resonator (TFR) Low Insertion Loss Filters; G.R. Kline, K.M. Lakin, and R.S. Ketcham; 1987 Ultrasonics Symposium Proceeding.

Growth and Characterization of Aluminum Nitride Thin Films for Piezoelectric Devises; K.T. McCarron, G.R. Kline, J.T. Martin, and K.M. Lakin; Presented at the 1988 Ultrasonics Symposium.

Non–Linear Modeling and Performance of Oscillators Using Thin–Film Bulk–Acoustic Wave Devices; S.G. Burns, P.H. Thompson, and G.R. Kline; Presented at the Frequency Control Symposium on Jun. 2, 1988.

Performance of TFR Filters Under Elevated Power Conditions, R.S. Ketcham, G.R. Kline, and K.M. Lakin; 42nd Annual Frequency Control Symposium—1988.

Thin Film Resonator Technology; K.M. Lakin, R.S. Ketchan, G.R. Kline, and R.J. Weber.

Design, Analysis, and Performance of UHF Oscillators Using Thin–Film Resonator–Based Devices as the Feedback Element; Stanley G. Burns and Philip H. Thompson; IEEE Midwest Symposium on Circuits and Systems (Aug. 1989).

Stacked Crystal Filters Implemented With Thin Films, K.M. Lakin, G.R. Kline, R.S. Ketcham, J.T. Martin, and K.T. McCarron; 43rd Annual Symposium on Frequency Control—1989, pp. 535–543.

Characterization of a Quartz Crystal Microbalance with Simultaneous Mass and Liquid Loading; Stephen J. Martin, Victoria Edwards Granstaff, and Gregory C. Frye; Analytical Chemistry, vol. 63, No. 20, Oct. 15, 1991, pp. 2272–2281.

Resonator/Oscillator Response to Liquid Loading; J.J. Spates, S.J. Martin, and R.J. Huber.

Thermodynamically Controlled Electrochemical Formation of Thiolate Monolayers at Gold: Characterization and Comparison to Self–Assembled Analogs; Duane E. Weisshaar, Brian D. Lamp, and Marc D. Porter; Journal of the American Chemical Society, vol. 114, No. 14, Jul. 1, 1992, pp. 5860–5862.

Applications of AlN Thin–Film Resonator Topologies As Antennas and Sensors; Robert J. Weber, Stanley G. Burns, Charles F. Campbell, Ron O'Toole; 1992 IEEE MTT–S Digest, pp. 161–164.

Operation of an Ultrasensitive 30–MHz Quartz Crystal Microbalance in Liquids; Zuxuan Lin, Christopher M. Yip, I. Scott Joseph, and Michael D. Ward; Analytical Chemistry, vol. 65, No. 11, Jun. 1, 1993, pp. 1546–1551.

Two–Dimensional Imaging of $O_2$, $H_2O_2$, and Glucose Distributions by an Array of 400 Individually Addressable Microelectrodes; Heinrich Meyer, Heinz Drewer, Bernd Grundig, Karl Cammann, Ralf Kaderow, Yiannos Manoli, Wilfried Mokwa, Matthias Respert; Analytical Chemistry, vol. 67, No. 7, Apr. 1, 1995, pp. 1164–1170.

The quartz crystal microbalance as biosensor, A Status Report on its Future; Analytical Letters, 28(5), 1995, pp. 749–764.

Qyartz crystal microbalance detection of Vibrio cholerae O139 serotype; R.M. Carter, J.J. Mekalanos, M.B. Jacobs, G.J. Lubrano, C.G. Guilbault; Journal of Immunological Methods 7515 (1995) xxxC, pp. 1–5.

Development and performance of a semiautomated 200 MHz surface acoustic wave resonator array–based sensor test apparatus; E.B. Townsent IV, J.S. Ledford, D.P. Hoffman; Rev. Sci. Instrum, vol. 66, No. 4, Apr. 1995, pp. 2954–2959.

A Biosensor Array Based on Polyaniline; H.Sangodkar, S. Sukeerthi, R.S. Srinivasa, R. Lai, and A.Q. Contractor; Analytical Chemistry, vol. 68, No. 5, Mar. 1, 1996, pp. 779–783.

METHOD AND SYSTEM FOR DETECTING MATERIAL USING PIEZOELECTRIC RESONATORS

FIELD OF THE INVENTION

This invention relates generally to sensors for detecting small quantities of materials, and more particularly to material sensors based on piezoelectric resonators.

BACKGROUND OF THE INVENTION

Resonators based on piezoelectric properties of materials have been used in many important applications. For instance, quartz crystal resonators are widely used as frequency control elements in oscillator circuits found in many devices such as computers and watches. They are also used as bulk-acoustic wave filters in a variety of circuits for frequency selection purposes.

One important application of piezoelectric resonators is in detecting very small quantities of materials. Piezoelectric resonators used as sensors in such applications are sometimes called "micro-balances." A piezoelectric resonator is typically constructed as a thin planar layer of crystalline piezoelectric material sandwiched between two electrode layers. When used as a sensor, the resonator is exposed to the material being detected to allow the material to bind on a surface of the resonator.

The conventional way of detecting the amount of the material bound on the surface of a sensing resonator is to operate the resonator as an oscillator at its resonant frequency. As the material being detected binds on the resonator surface, the oscillation frequency of the resonator is reduced. The change in the oscillation frequency of the resonator, presumably caused by the binding of the material on the resonator surface, is measured and used to calculate the amount of the material bound on the resonator or the rate at which the material accumulates on the resonator surface.

The sensitivity of a piezoelectric resonator as a material sensor is typically proportional to its resonance frequency. Thus, the sensitivities of material sensors based on the popular quartz crystal resonators are limited by their relatively low oscillating frequencies, which typically range from several MHz to about 100 MHz. The recent development of thin-film resonator (TFR) technology has produced sensors with significantly improved sensitivities. A thin-film resonator is formed by depositing a thin film of piezoelectric material, such as AlN or ZnO, on a substrate. Due to the small thickness of the piezoelectric layer in a thin-film resonator, which is on the order of several microns ($\mu$m), the resonant frequency of the thin-film resonator is on the order of 1 GHz or higher. The high resonant frequencies and the corresponding high sensitivities make thin-film resonators useful for material sensing applications.

The conventional method of detecting material by measuring a change in the oscillation frequency of the sensing resonator requires the incorporation of the sensing resonator in an oscillator circuit to drive the sensing resonator into oscillation. To obtain accurate measurement results, the oscillator circuit has to be stable and frequency matched to the resonant frequency of the sensing resonator. This requirement, however, is difficult to satisfy in practice. Many applications use sensors of a disposable type, i.e., sensors have to be replaced from time to time. In such a case, the same electronics will be used with many sensing resonators. Nevertheless, due to variations in the fabrication process, the sensing resonators may have significantly different resonant characteristics. For instance, the non-uniformity in the deposition thickness of a piezoelectric layer deposited across a substrate can cause the resonance frequencies of thin-film resonators from the same production batch to vary significantly. As a result, a non-adjustable oscillator circuit is incapable of effectively driving all of the sensing resonators into oscillation. It is possible to use external tuning elements to fine tune an oscillator circuit to match the resonant characteristics of individual sensing resonators. The use of tuning elements, however, can significantly increase undesirable phase noise. Moreover, fine tuning the oscillator circuit to match the sensing resonators is not feasible in practice for field applications.

Another significant disadvantage of the conventional approach is the difficulty in separating the real signal from spurious environmental effects. During material detection, a sensing resonator is often exposed to different environmental conditions that also tend to alter the oscillation frequency of the resonator. It is often difficult to isolate the frequency change caused by the material detected from the frequency changes caused by various environmental conditions.

SUMMARY OF THE INVENTION

In view of the foregoing, it is a primary object of the present invention to provide a method and system for detecting materials using piezoelectric resonators that effectively avoids the difficulties in matching oscillator circuits to the resonant characteristics of individual sensing resonators.

It is a resultant object of the invention to provide a method and system of detecting material with piezoelectric resonators that does not require the incorporation of sensing resonators in oscillator circuits.

It is a related object of the invention to provide a method and system for detecting material with piezoelectric resonators that does not use the conventional approach of incorporating the sensing resonators into oscillator circuits and is capable of providing high measurement sensitivity, stability, and ease of operation.

It is a further related object of the present invention to provide a method and system for detecting materials with piezoelectric resonators that does not require the use of the resonators in oscillator circuits and operates in a way that allows effective separation of the desired signal from environmental effects.

It is an object of the invention to provide a piezoelectric sensing device suitable for a method and system for detecting materials that does not require the use of sensing resonators in oscillator circuits.

In accordance with these and other objects of the invention, there is provided a method and system for detecting material using a sensing resonator that measures a change in insertion phase shift of the resonator caused by the binding of the material being detected on a surface of the resonator. An input electrical signal having a frequency within a resonance band of the piezoelectric resonator is coupled to and transmitted through the resonator to generate an output electrical signal which is phase-shifted from the input signal due to the insertion of the resonator in the signal path. The insertion phase shift is altered when the material being detected binds on the resonator surface. The output electrical signal received from the piezoelectric resonator is analyzed to determine the change in insertion phase shift caused by the binding of the material on the resonator surface. The measured change in insertion phase shift provides quantitative information regarding the material bound to the resonator surface.

It is a feature of the present invention to detect material binding on a sensing resonator by measuring the change in insertion phase shift, in contrast to the conventional approach of operating the sensing resonator as an oscillator and detecting a change in the oscillation frequency. Thus, the need for tuned oscillator circuits is entirely eliminated, and therewith the problem of matching oscillator circuits with different sensing resonators. One of the important advantages of the phase shift detection according to the invention is that the input electrical signal is kept at a constant frequency during the measurement. The constant frequency of the input signal provides a baseline of the measurement, and there is no longer the need to follow an ever changing oscillation frequency as in the conventional method.

Another advantage of the phase detection according to the invention is the simplification of the electronics for the sensing system. Because the input signal is kept constant during measurement, simple and inexpensive signal sources with adjustable output frequencies, such as frequency synthesizers, can be used.

Another significant advantage of the phase detection approach is that one signal source can be used to provide input signals simultaneously to multiple resonators. As a result, a reference resonator may be used in conjunction with a sensing resonator to effectively separate environmental effects from the phase shift change caused by the binding of the material being detected on the sensing resonator.

The phase detection approach of the invention can be advantageously used with different types of sensing resonators in different configurations. For instance, both the conventional quartz crystal resonators and the newer thin-film resonators can be used as sensors, and the sensing resonator may be configured as a one-port or two-port device. Depending on the applications, the resonators in the sensor may operate in longitudinal or shear modes.

In a particularly advantageous embodiment, a thin-film sensing device includes a reference resonator and at least one sensing resonator monolithically formed on a substrate. The input electrical signal is coupled to the electrodes of the reference and sensing resonators via a transmission line and a power divider. The close proximity of the reference and sensing resonators allows the resonators to be fabricated with closely matched resonant characteristics, which allow effective cancellation of environmental effects during material sensing operations.

Other objects and advantages will become apparent with reference to the following detailed description when taken in conjunction with the drawings in which:

Figure 1A:
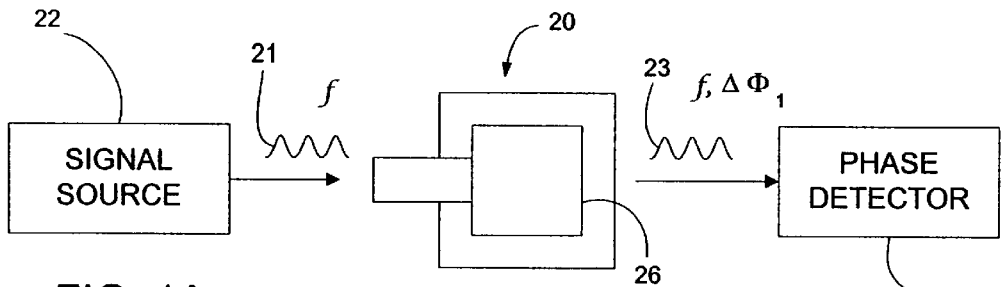
FIGS. 1A and 1B are schematic diagrams illustrating the operational principles of the invention.

While the invention is susceptible of various modifications and alternative constructions, certain illustrated embodiments hereof have been shown in the drawings and will be described below. It should be understood, however, that there is no intention to limit the invention to the specific forms disclosed, but, on the contrary, the intention is to cover all modifications, alternative constructions and equivalents falling within the spirit and scope of the invention as defined by the appended claims.

DETAILED DESCRIPTION OF THE PREFERRED EMBODIMENT

Figure 1B:
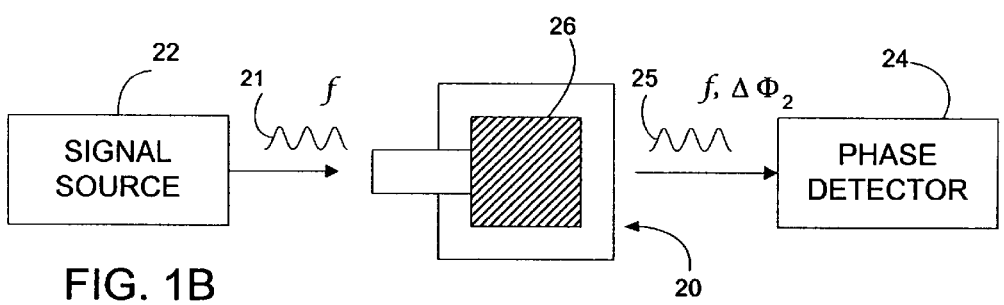

Turning now to the drawings, the general operating principles of the invention are illustrated with the aid of FIGS. 1A and 1B. Generally, a bulk-acoustic wave piezoelectric resonator 20 is used as a sensor to detect the existence of a given material. The resonator 20 typically includes a planar layer of piezoelectric material bounded on opposite sides by two respective metal layers which form the electrodes of the resonator. The two surfaces of the resonator are free to undergo vibrational movement when the resonator is driven by a signal within the resonance band of the resonator. When the resonator is used as a sensor, at least one of its surfaces is adapted to provide binding sites for the material being detected. The binding of the material on the surface of the resonator alters the resonant characteristics of the resonator, and the changes in the resonant characteristics are detected and interpreted to provide quantitative information regarding the material being detected.

It is a feature of the present invention to derive such quantitative information by detecting a change in the insertion phase shift of the resonator caused by the binding of the material being detected on the surface of the resonator. In contrast to the conventional approach of operating the resonator as an oscillator and monitoring changes in the oscillation frequency, the present invention inserts the resonator in the path of a signal of a pre-selected constant frequency, and monitors the variation of the insertion phase shift caused by the binding of the material being detected on the resonator surface.

In more detail, FIG. 1A shows the resonator 20 before the material being detected is bound to its surface 26. The resonator 20 is electrically coupled to a signal source 22, which provides an input electrical signal 21 having a frequency f within the resonance band of the resonator. The input electrical signal is coupled to the resonator 20 and transmitted through the resonator to provide an output electrical signal 23. The output electrical signal 23 is at the same frequency as the input signal 21, but differs in phase from the input signal by a phase shift $\Delta\phi_1$, which depends on the piezoelectric properties and physical dimensions of the resonator. The output signal 23 is coupled to a phase detector 24 which provides a phase signal related to the insertion phase shift.

FIG. 1B shows the sensing resonator 20 with the material being detected bound on its surface 26. The same input signal is coupled to the resonator 20. Because the resonant characteristics of the resonator are altered by the binding of the material as a perturbation, the insertion phase shift of the output signal 25 is changed to $\Delta\phi_2$. The change in insertion phase shift caused by the binding of the material is detected by the phase detector 24. The measured phase shift change is related to the amount of the material bound on the surface of the resonator.

This phase detection approach of the invention can be advantageously used with piezoelectric resonators of different resonant frequencies and configurations. For example, the sensing resonators may be conventional quartz resonators or the more recently developed thin-film resonators. Nevertheless, thin-film resonators are generally preferred because of their high resonance frequencies and the accompanying higher sensitivities. Depending on the applications, a thin-film resonator used as the sensing element may be formed to support either longitudinal or shear bulk-acoustic wave resonant modes. Longitudinal-mode TFR sensors can be effectively used in a vacuum or gaseous environment. On the other hand, shear-mode TFR sensors are more suitable for use in a liquid sample. This is because a longitudinal-mode resonance is severely damped by the presence of liquid at the surface, while a shear mode resonance is only partially damped.

Figure 2:
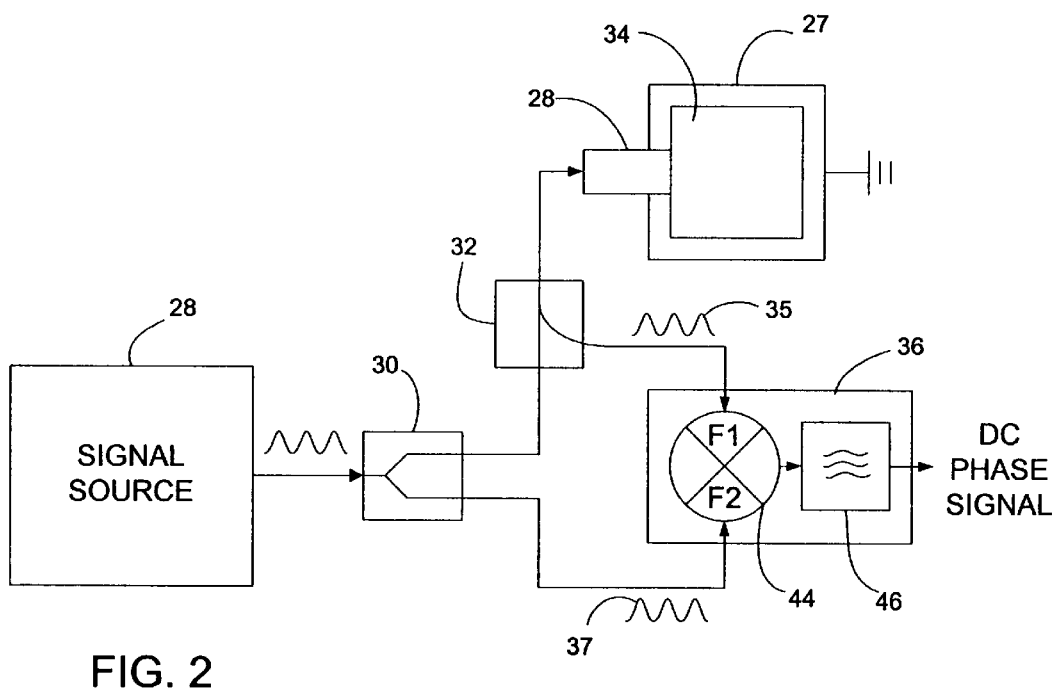
FIG. 2 is a schematic diagram of a material sensing system having a one-port resonator as a sensor.

FIG. 2 shows a simple sensor system embodying the invention that has a one-port resonator 27 as the sensing element. A one-port resonator has one electrode that is used for both signal input and output. The other electrode of the one-port resonator is typically grounded. As illustrated in FIG. 2, a signal source 28 provides an input signal which has a frequency within the resonant bandwidth of the sensing resonator 27. The input signal is coupled to a power divider 30, which splits the input signal into two portions. One portion of the input signal is sent through a coupler 32 to the input/output electrode 29 of the resonator 27.

The input signal is transmitted across the resonator 27 and reflected back to the electrode 29. The output signal, i.e., the reflected signal which has an insertion phase shift with respect to the input signal, is then conducted to the coupler 32. The coupler 32 is a directional device that is capable of separating the output signal from the input signal. The output signal is directed by the coupler 32 to a phase detector 36 as a sensor signal 35. The second portion of the input signal is also sent from the power divider 30 to the phase detector 36 as a reference signal 37. The phase detector 36 processes the sensor signal and the reference signal to provide a phase signal indicative of a phase difference between the sensor and reference signals.

In a sensing operation, the sensing resonator is exposed to the material being detected, and the insertion phase shift changes as a result of the binding of the material on the surface of the resonator 27. This change is reflected in the phase signal generated by the phase detector 36.

One of the important advantages of the phase detection approach of the invention is that the input signal is maintained at a pre-selected constant frequency during measurement. A stable signal source with an adjustable signal frequency is relatively simple and inexpensive to construct, in contrast to the rather complicated and expensive temperature-compensated high-frequency oscillator circuitry required by the conventional approach of tracking the changing oscillation frequency of the resonator. As an example, the signal source 28 may be a frequency synthesizer. Frequency synthesizers are relatively inexpensive and readily available.

The phase detector 36 in the illustrated embodiment includes a double-balanced mixer 44 (or a mathematical multiplier) which receives the sensor and reference signals. The sensor signal and the reference signal can be expressed respectively as $A_{sen}\cos(\omega t)$ and $A_{ref}\cos(\omega t - \Delta\phi)$, where $\Delta\phi$ is the phase difference between the sensor signal and the reference signal. The mixer 44 multiplies the sensor signal and the reference signal to produce a signal $$A_{det}(t) = L(A_{sen}A_{ref})\cos(\omega t - \Delta\phi)$$

$$= L(A_{sen}A_{ref})(1/2)\{\cos(\Delta\phi) + \cos(2\omega t - \Delta\phi)\},$$

where $L(A_{sen}A_{ref})$ is a generic loss function. During a sensing operation, the output power of the signal source 28 is kept constant. The loss function $L(A_{sen}A_{ref})$ is therefore a constant. The term $L(A_{sen}A_{ref})(\frac{1}{2})\cos(\Delta\phi)$ varies with the phase difference, $\Delta\phi$, but does not vary with time, i.e., it is a DC term. The output of the mixer 44 is passed through a low-pass filter 46 which eliminates the time dependent term in $A_{det}$ and leaves only the DC term as the output of the phase detector 36. In this way, the phase detector provides a DC voltage signal indicative of a phase difference between the sensor signal and the reference signal. The measured phase shift change can be used to derive the total amount of the material bound on the surface of the sensing resonator. Alternatively, the DC voltage signal can be monitored as a function of time to determine the rate at which the insertion phase shift changes. This rate of change relates to the rate at which the material being detected binds to the surface of the sensing resonator 27. If the resonator is used in an aqueous environment, the rate of change provides an indication of the concentration or density of the material being detected in the liquid.

In many applications, the exposure of a sensing resonator to the material being detected involves subjecting the resonator to different environmental conditions which can also alter the resonant characteristics of the resonator. For instance, when used as a thickness monitor in an epitaxial deposition operation, the resonator is often subjected to heat which could shift the resonance frequency. As another example, if the resonator is submerged in a liquid to detect the existence of certain molecules in the liquid, the contact of the surface with the liquid also introduces certain viscosity loading effects that are separate from the effects caused by the binding of the molecules on the surface. Such environmental effects can mask the phase change caused by the material being detected and generate erroneous results.

In accordance with an aspect of the invention, such environmental effects are effectively distinguished from the material binding effects by the use of a reference resonator. The reference resonator preferably has resonant characteristics sufficiently close to those of the sensing resonator so that the phase shifts of the two resonators caused by the environmental effects are very similar in magnitude. During the sensing operation, the sensing and reference resonators are subject to substantially identical environmental conditions. Nevertheless, the material to be detected is prevented from binding on the surface of the reference resonator. This can be achieved by blocking the surface of the reference resonator from the material being detected, or by coating only the sensing resonator to provide the needed binding sites for the material. Due to the similar resonant characteristics of the sensing and reference resonators, the environmental conditions are expected to cause substantially the same insertion phase shift change in the two resonators. Since the material being detected does not bind on the reference resonator, the phase shift change of the reference resonator reflects mainly the environmental effects. The phase shift change of the reference resonator is subtracted from the total phase shift change of the sensing resonator to provide a difference signal which reflects mainly the material binding effects.

Figure 3:
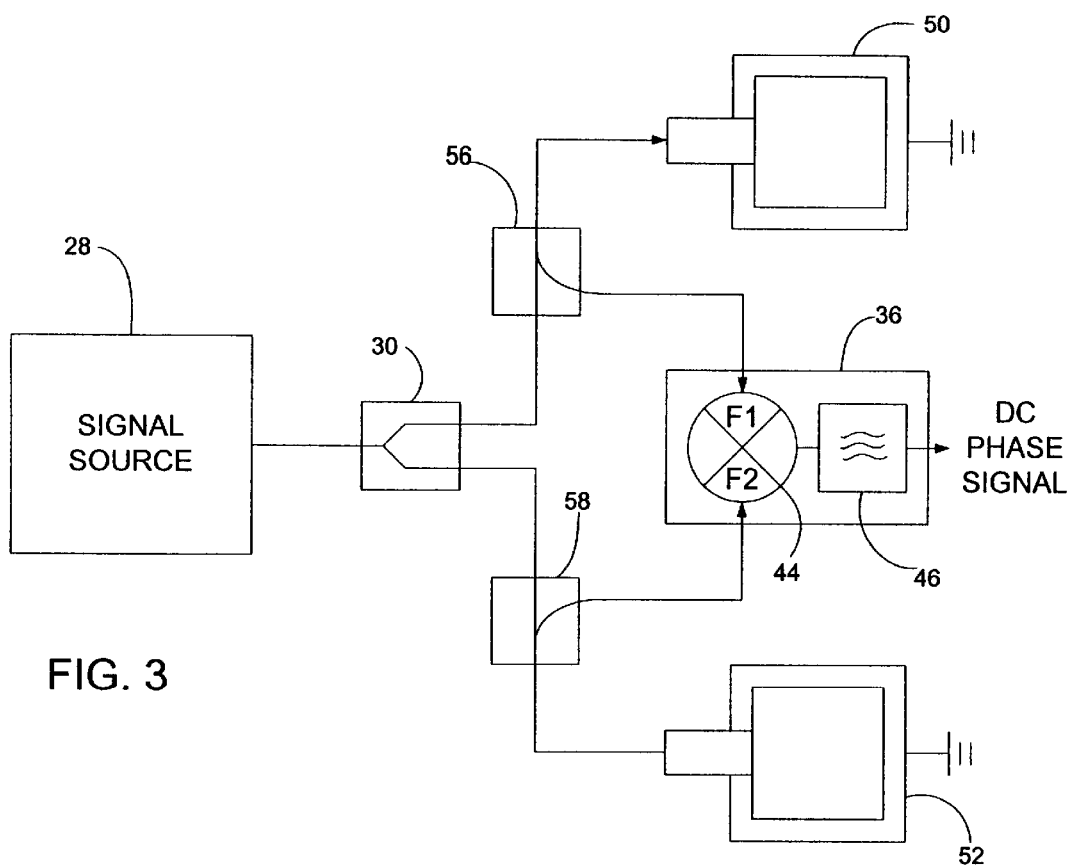
FIG. 3 is a schematic diagram of a material sensing system having a one-port sensing resonator and a one-port reference resonator.

FIG. 3 shows a sensing system which has a one-port sensing resonator 50 and a one-port reference resonator 52.

The signal source, power divider, and phase detector used in this system are identical to those in the system of FIG. 2 and are therefore identically numbered. The sensing resonator 50 and the reference resonator 52 preferably have very similar resonant characteristics and substantially overlapping resonant bands. The signal source 28 provides an input signal of a frequency which is within the overlapping portion of the resonant bands of the resonators and preferably is set equal to the average of the resonance frequencies of the two resonators. The input electrical signal provided by the signal source 28 is split by a power divider 30 and the split signals are coupled through couplers 56, 58 to the respective sensing and reference resonators 50, 52. The output signals of the resonators are directed to the phase detector 36 by the respective couplers 56, 58 as sensor and reference signals. The phase detector 36 processes the sensor and reference signals to produce a phase signal indicative of a phase difference between the two signals. As described above, this phase difference is expected to be caused mainly by the binding of the material being detected on the surface of the sensing resonator 50.

Figure 4:
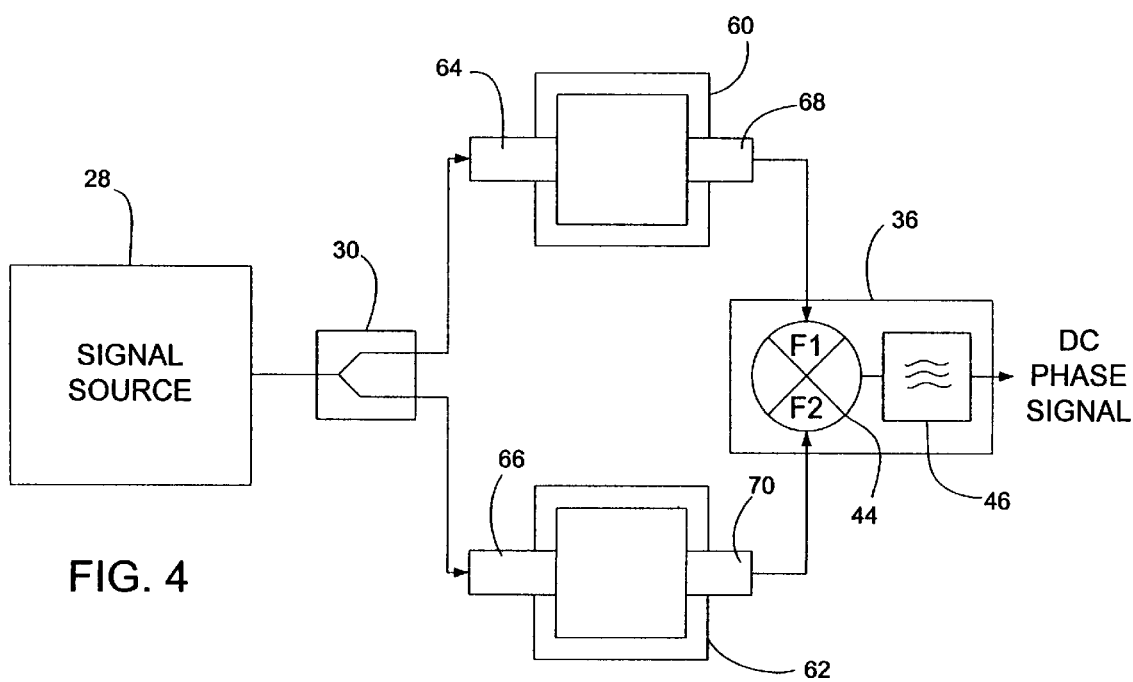
FIG. 4 is a schematic diagram of a material sensing system with two-port sensing and reference resonators.

The phase detection according to the invention can also be advantageously implemented with two-port resonators. A two-port resonator has one electrode for receiving an input signal, and a second electrode for providing an output signal. FIG. 4 shows a sensing system which has a two-port sensing resonator 60 and a two-port reference resonator 62. The sensing and reference resonators preferably have very similar resonant characteristics, and the resonant bands of the two resonators substantially overlap with each other. A signal source 28 provides an input electrical signal which has a frequency within the overlapping portion of the resonant band of the two resonators. The input signal is split by a power divider 30, and the split signals are coupled to the respective input electrodes 64, 66 of the sensing and reference resonators 60, 62. The input signals are transmitted through the resonators to form output electrical signals at the respective output electrodes 68, 70 of the sensing and reference resonators. The output signals of the two resonators are coupled to the phase detector 36, which produces a phase signal indicative of a phase difference between the two output signals. Quantitative information of the material bound on the surface of the sensing resonator can then be derived from the phase signal.

Figure 5A:
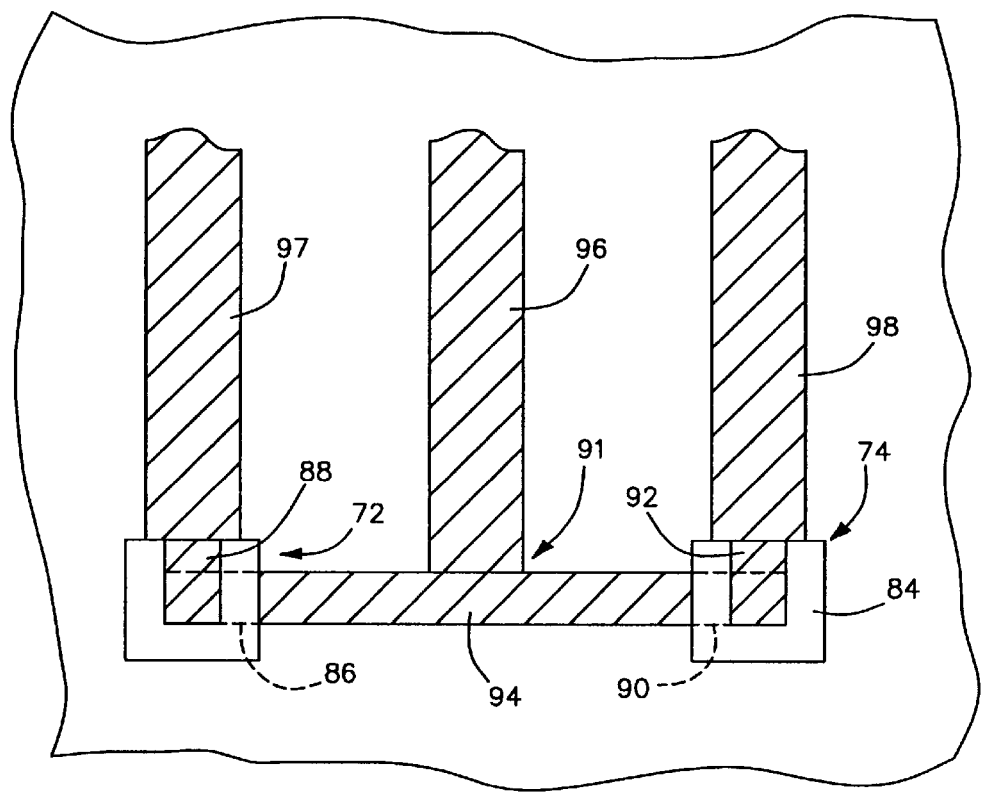
FIGS. 5A and 5B are schematic top and cross sectional views, respectively, of a three-port sensor having thin-film sensing and reference resonators monolithically formed on a substrate.
Figure 5B:
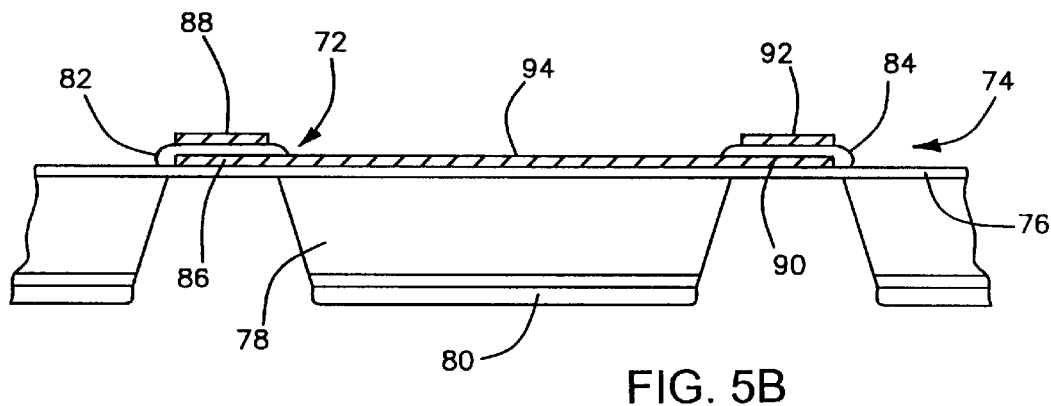

In a particularly advantageous embodiment of the invention, the two-port reference/sensing resonator combination described above is implemented as a monolithically fabricated three-port device which comprises basically two two-port thin-film resonators with their input electrodes connected to a common input. As illustrated in FIGS. 5A and 5B, the two resonators 72, 74 are supported on a thin $SiO_2$ layer 76 which is thermally grown on a silicon substrate 78. The $SiO_2$ layer 76 has a thickness of about 1000 Å. The Si substrate 78 has thickness of about 345 $\mu$m, a width of 4 mm and a length of 12 mm. The portions of the Si substrate under the resonators are etched away to allow the resonators to undergo resonant movement. The bottom of the Si substrate 78 has a layer of silver paint 80 applied thereto which serves as a grounding plane.

In the illustrated embodiment, the resonator 72 has an epitaxially deposited AlN layer 82 grown to a thickness of about 2.35 $\mu$m to provide a shear mode resonance frequency of 900 MHz. Alternatively, the piezoelectric layer may be formed of ZnO. The AlN layer 82 is in the shape of a square of side width of 500 $\mu$m. A rectangular input electrode 86 and a rectangular output electrode 88 are formed on opposite sides of the piezoelectric layer 82. Each of the electrodes 86, 88 is a 0.5 $\mu$m thick Al layer. The width of the electrodes is about 200 $\mu$m. The overlapping portion of the two electrodes 86, 88 defines a square active area of the resonator 72, which is about 200 $\mu$m by 200 $\mu$m. The size of the active area of the resonator is selected to keep the static capacitance of the resonator sufficiently small to avoid distortion of the phase response of the resonator around resonance. With the chosen size and thickness of the active area of the resonator, the static capacitance is about 0.64 pF.

The other resonator 74 is generally a mirror image of the resonator 72, with an AlN layer 84 formed between an input electrode 90 and an output electrode 92. Due to the symmetry of the two resonators, either resonator can be prepared, such as by applying a proper coating, for use as the sensing resonator. The other resonator is then used as the reference resonator.

The input electrical signal is coupled to the two resonators via a transmission line 96 formed on the substrate. The transmission line 96 is a deposited Al strip which has a width of 277 $\mu$m and a thickness of 0.5 $\mu$m. The dimensions of the transmission line are chosen to provide a 50 Q impedance on the Si substrate. Similar transmission lines 97, 98 are connected to the output electrodes 88, 92 of the two resonators 72, 74, respectively, for coupling the respective output signals to a phase detector.

The transmission line 96 conducts the input electrical signal to a power divider 91 which splits the input electrical signal into two portions. The split signals are conducted to the respective input electrodes 86, 90 of the two resonators by a deposited Al strip 94 which has the same width as the input electrodes. In the illustrated embodiment, the power divider 91 is in the form of a T-junction of the transmission line 96 and the connecting strip 94. This T-junction power divider is simple in structure and easy to fabricate. Nevertheless, other types of power dividers may also be used. For example, the T-junction may be replaced by a Wilkinson power divider which is only slightly more complicated in design but provides better isolation between the two resonators.

It is an important advantage of the embodiment that the two resonators are disposed close to each other on the same substrate. The proximity ensures that the two resonators are subjected to substantially identical environmental conditions during a material sensing operation. On the other hand, sufficient distance should be provided to reduce cross talk between the two resonators. In the illustrated embodiment, the centers of the two resonators are separated by about 2000 $\mu$m.

Another important advantage of forming the sensing and reference sensors in close proximity on the same substrate is that the two resonators are likely to have closely matched resonant frequencies and phase responses. The matched phase responses allow accurate phase shift measurements and effective cancellation of environmental effects.

It will be appreciated by those skilled in the art that the general structure of the monolithic sensing/reference resonator combination described above can be used to fabricate sensing devices with more than two resonators on a given substrate. For instance, two or more three-port TFR devices each having a sensing resonator and a reference resonator can be monolithically fabricated on one substrate. During a sensing operation, the output of the sensing resonator in each three-port device can be referenced to the output of the reference resonator in the same device. Alternatively, the sensor can be formed as a multiple-port device with one reference resonator and two or more sensing resonators, with the input electrodes of the resonators connected to a common signal input. During a sensing operation, the output of each of the sensing resonators is referenced to the output of the reference resonator.

It will also be appreciated that other types of TFR structures may be used to fabricate multiple-resonator sensors for use with the phase detection technique of the invention. For instance, a resonator network illustrated in FIG. 7A of U.S. Pat. No. 5,231,327 to Ketcham includes two resonators which share a common input electrode. One of the resonators may be used as the reference resonator, and the other the sensing resonator. The '327 patent is hereby incorporated by reference.

Figure 6A:
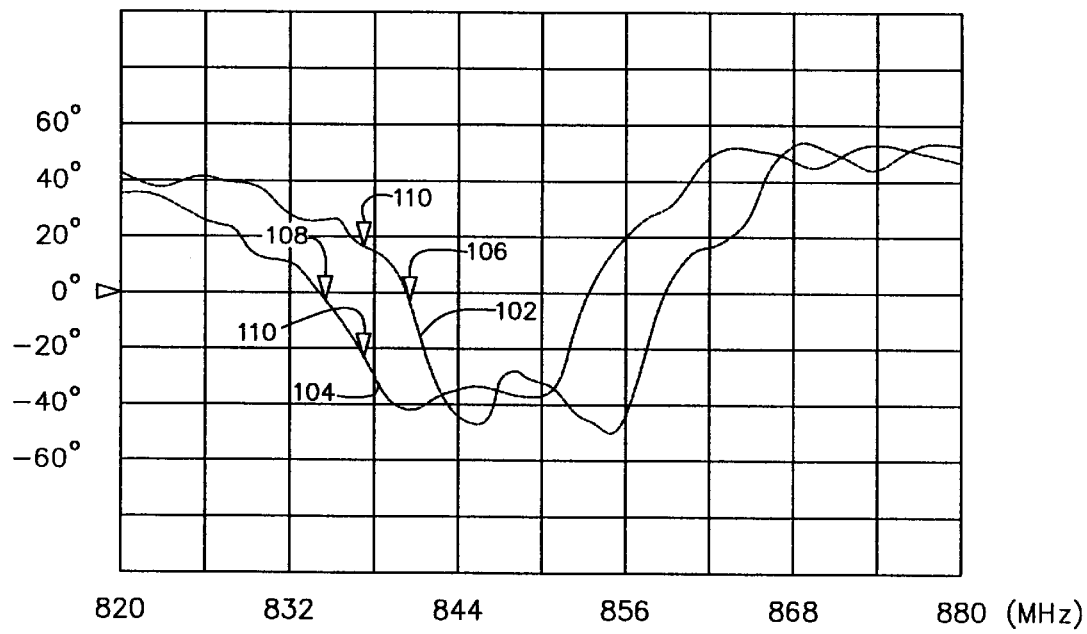
FIG. 6A shows measured insertion phase curves of a sensing resonator and a reference resonator before a material detection operation.
Figure 6B:
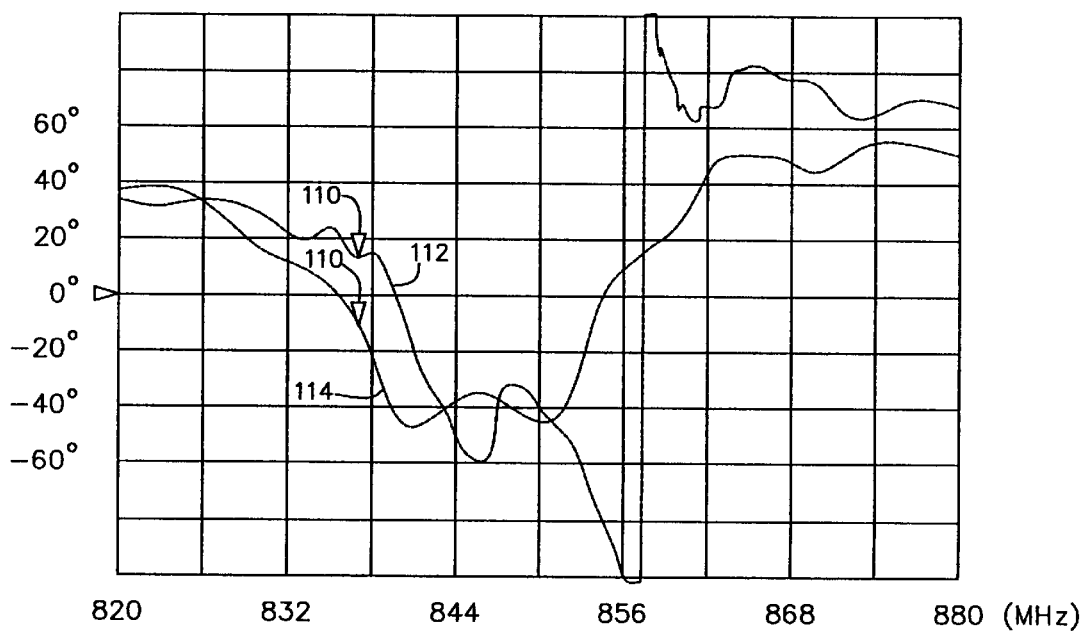
FIG. 6B shows measured insertion phase curves of the sensing and reference resonators of FIG. 6A after the material detection operation.

To further illustrate the operating principles of the invention, FIGS. 6A and 6B show measured results taken with a longitudinal-mode three-port TFR sensing device which has a sensing resonator and a reference resonator arranged in the general structure shown in FIGS. 5A and 5B. The sensor was used to detect Listeria bacteria in an aqueous sample. For that purpose, the surface of the sensing resonator was coated with the antibody for the Listeria bacteria. The antibody molecules provided strong binding sites for the bacteria. The surface of the reference sensor was coated with a different antibody which was not expected to have significant binding with the Listeria bacteria in the liquid sample.

FIG. 6A shows the phase curves 102, 104 region for the sensing and reference resonators, respectively, taken before the sensing operation. The resonance frequency of the sensing resonator was 840.1 MHz, as indicated by the marker 106, and the resonance frequency of the reference resonator was 834.5 MHz, as indicated by the marker 108. It can be seen that the phase bands of the two resonators have significant overlap.

The sensor was used in the phase detection system of FIG. 4. The frequency of the input electric signal for the two resonators was set close to 837.25 MHz (indicated by the marker 110), which was about the medium of the resonant frequencies of the two resonators. At that frequency, the insertion phase difference between the sensing and reference resonators was about 41 degrees.

The three-port sensor was then submerged in the liquid sample containing the material to be detected, namely Listeria bacteria. The sensor was left in the liquid for 5 minutes to allow the bacteria to bind to the antibody-coated surface of the sensing resonator. Subsequently the sensor was removed from the solution, rinsed to remove unbound Listeria bacteria and then air dried. FIG. 6B shows the measured phase curves 112, 114 of the two resonators after this binding procedure. It will be appreciated that the phase curves of the resonators are provided in FIGS. 6A and 6B only for the purpose of illustrating the operating principles of the invention. If the sensing system of FIG. 4 is used, it will not be necessary to scan over the entire resonance region. Instead, the input signal will be set at a constant frequency, such as 837.25 MHz, and the phase difference between the resonators at that frequency will be detected and indicated by the phase signal generated by the phase detector.

As can be seen in FIGS. 6A and 6B, the phase difference between the sensing resonator and the reference resonator was altered by the binding process. At the input signal frequency of 837.25 MHz indicated by the marker 110, the phase difference between the two resonators was reduced to about 30 degrees. Thus, the binding of the material being detected on the surface of the sensing resonator changed the insertion phase difference by about 11 degrees at the selected input frequency of 837.25 MHz.

It should now become appreciated that what is provided is a method and system for sensing a given material with a piezoelectric sensor that transmits a constant-frequency input signal through the sensing resonator and measures changes in the insertion phase shift, which are caused by the binding of the material being detected on the sensing resonator. The insertion phase shift change provides quantitative information of the material being detected. By virtue of the constant signal frequency in the phase detection, simple and inexpensive input signal sources can be used. The phase detection approach also allows effective cancellation of environmental effects on the measurement by the use of a reference resonator driven by the same input electrical signal. In the preferred embodiment, the sensing and reference resonators are monolithically formed as a thin-film multiple-port sensing device. The monolithic construction ensures close matching of the resonant characteristics of the sensing and reference resonators, thereby allowing accurate measurement and effective cancellation of environmental effects.

What is claimed is:

1. A method of detecting binding of material on a surface of a piezoelectric resonator operable in a bulk-acoustic wave resonant mode, comprising the steps of:

coupling an input electrical signal to the piezoelectric resonator, the input electric signal having a frequency within a resonance band of the piezoelectric resonator;

transmitting the input electrical signal through the piezoelectric resonator to generate an output electrical signal having a frequency identical to the frequency of the input electrical signal;

receiving the output electrical signal from the piezoelectric resonator; and determining a change in insertion phase shift of the output electrical signal caused by binding of the material on the surface of the piezoelectric resonator, whereby the change in insertion phase shift provides quantitative information regarding the binding of the material on the surface of the piezoelectric resonator.

2. A method as in claim 1, wherein the step of determining includes deriving a rate of change of the insertion phase shift, said rate of change indicative of a concentration of the material being detected.

3. A method as in claim 1, wherein the piezoelectric resonator is a thin-film resonator.

4. A method as in claim 3, wherein the thin-film resonator is formed of AlN.

5. A method as in claim 3, wherein the thin-film resonator is formed of ZnO.

6. A method as in claim 1, wherein the step of coupling transmits the input electrical signal to an electrode of the piezoelectric resonator, and wherein the step of receiving receives the output electrical signal from said electrode.

7. A method as in claim 1, wherein the step of transmitting transmits the input electrical signal to a first electrode of the piezoelectric resonator, and wherein the step of receiving receives the output electrical signal from a second electrode of the piezoelectric resonator.

8. A method as in claim 1, wherein the bulk-acoustic wave resonant mode is a shear mode.

9. A method as in claim 1, wherein the bulk-acoustic wave resonant mode is a longitudinal mode.

10. A method as in claim 1, wherein the step of determining includes mixing the output electrical signal with a reference signal and providing a DC signal proportional to a phase difference between the output electrical signal and the reference signal.

11. An apparatus for detecting material comprising:
- a piezoelectric resonator operable in a bulk-acoustic wave resonant mode and having a surface for binding with the material being detected;
- a signal source for generating an input electrical signal having a frequency within a resonance band of the piezoelectric resonator, the signal source coupled to the piezoelectric resonator for transmitting the input electrical signal through the piezoelectric resonator to generate an output electrical signal having a frequency identical to the frequency of the input electrical signal;
- a phase detector coupled to the piezoelectric resonator for receiving therefrom the output electrical signal and generating a phase signal indicative of a change in insertion phase shift of the piezoelectric resonator caused by binding of the material on the surface of the piezoelectric resonator.

12. An apparatus as in claim 11, wherein the piezoelectric resonator is a thin film resonator.

13. An apparatus as in claim 12, wherein the thin film resonator is formed of AlN.

14. An apparatus as in claim 12, wherein the thin-film resonator is formed of ZnO.

15. An apparatus as in claim 11, wherein the phase signal generated by the phase detector is a DC voltage indicative of the change in insertion phase shift.

16. An apparatus as in claim 11, wherein the bulk-acoustic wave resonant mode of the piezoelectric resonator is a shear mode.

17. An apparatus as in claim 11, wherein the bulk-acoustic wave resonant mode of the piezoelectric resonator is a longitudinal mode.

18. An apparatus for material detection comprising:
- a reference resonator and at least one sensing resonator supported for bulk-acoustic wave resonance, the reference resonator having a resonant band overlapping a resonant band of the sensing resonator, the sensing resonator having a surface for binding with the material being detected;
- a signal source providing an input signal having a frequency within an overlapping portion of the resonance bands of the reference resonator and the sensing resonator, the signal generator coupled to the reference resonator and the sensing resonator for transmitting the input signal therethrough to generate respectively a reference signal and a sensor signal each having a frequency identical to the frequency of the input signal;
- a phase detector coupled to the reference resonator and the sensing resonator to receive the reference signal and the sensor signal, the phase detector generating a phase signal representing a phase difference between the reference signal and the sensor signal, whereby the phase difference is altered by binding of the material on the surface of the sensing resonator.

19. An apparatus as in claim 18, wherein said reference resonator and at least one sensing resonator are thin film resonators monolithically formed on the substrate.

20. An apparatus as in claim 19, wherein the thin-film resonators are formed of AlN.

21. An apparatus as in claim 19, wherein the thin-film resonators are formed of ZnO.

22. An apparatus as in claim 18, wherein the reference resonator and the sensing resonator each has an input electrode coupled to the signal source for receiving the input signal and an output electrode connected to the phase detector to provide respectively the reference signal and the sensor signal.

23. An apparatus as in claim 18, wherein the input electrodes of the sensing resonator and the reference resonator are connected to a transmission line formed on the substrate for coupling the input signal to the respective resonators.

24. An apparatus as in claim 18, wherein each of the reference resonator and the sensing resonator operates in a longitudinal mode.

25. An apparatus as in claim 18, wherein each of the reference resonator and the sensing resonator operates in a shear mode.

26. A method of detecting material comprising the steps of:
- providing a sensing resonator and a reference resonator supported for bulk-acoustic wave resonance, the sensing resonator having a resonant band overlapping a resonant band of the reference resonator, the sensing resonator having a surface for binding with the material being detected; and
- generating an input signal within an overlapping portion of the resonant bands of the reference resonator and the sensing resonator;
- coupling the input signal to the reference resonator and the sensing resonator and transmitting the input signal therethrough to generate respectively a reference signal and a sensor signal each having a frequency identical to the frequency of the input signal;
- detecting a change in phase difference between the sensor signal and the reference signal in response to the binding of the material on the surface of the sensing resonator.

27. A method as in claim 26, wherein the step of detecting includes deriving a rate of change in phase difference between the sensor and reference signals.

28. A method as in claim 26, wherein the reference resonator and the sensing resonator are thin film resonators monolithically formed on a substrate.

29. A method as in claim 28, wherein the step of coupling couples the input signal to the reference resonator and the sensing resonator through a power divider formed on the substrate.

30. A method as in claim 26, wherein each of the reference resonator and the sensing resonator operates in a shear mode.

31. A method as in claim 26, wherein each of the reference resonator and the sensing resonator operates in a longitudinal mode.

32. A monolithic sensor for detecting adsorption of material comprising:
- a substrate layer;
- a reference resonator and at least one sensing resonator formed on the substrate layer and supported for bulk-acoustic wave resonance, each of the reference resonator and the sensing resonator having a thin-film piezoelectric layer and input and output electrodes on opposite sides of the piezoelectric layer, the reference resonator having a resonance band overlapping a resonance band of the sensing resonator;
- a first transmission line formed on the substrate layer for coupling an input electrical signal;
- a power divider connected to the first transmission line and the input electrodes of the reference resonator and the sensing resonator for directing the input electrical signal from the first transmission line to the reference and sensing resonators;
- a second transmission line formed on the substrate layer and connected to the output electrode of the reference resonator for delivering a reference signal generated by transmitting the input electrical signal through the reference resonator and having a frequency identical to the frequency of the input electrical signal; and a third transmission line formed on the substrate layer and connected to the output electrode of the sensing resonator for delivering a sensor signal generated by transmitting the input electrical signal through the sensing resonator and having a frequency identical to the frequency of the input electrical signal.

33. A monolithic sensor as in claim 32, wherein the thin-film piezoelectric layers of the reference resonator and the sensing resonator are formed of AlN.

34. A monolithic sensor as in claim 32, wherein the thin-film piezoelectric layers of the reference resonator and the sensing resonator are formed of ZnO.

35. A monolithic sensor as in claim 32, wherein each of the reference resonator and the sensing resonator operates in a shear mode.

36. A monolithic sensor as in claim 32, wherein each of the reference resonator and the sensing resonator operates in a longitudinal mode.

37. A monolithic sensor as in claim 32, wherein the power divider is a T-junction.

* * * * *